United States Patent
Briggs et al.

(10) Patent No.: US 6,220,258 B1
(45) Date of Patent: Apr. 24, 2001

(54) EXTRUDED PLASTIC TOOTHPICK AND METHOD

(76) Inventors: Robert B. Briggs; Gayle B. Bedigian, both of 8307 Brook Mere Blvd., Frederick, MD (US) 21702

( * ) Notice: Subject to any disclaimer, the term of this patent is extended or adjusted under 35 U.S.C. 154(b) by 0 days.

(21) Appl. No.: 09/523,272

(22) Filed: Mar. 10, 2000

Related U.S. Application Data

(60) Provisional application No. 60/124,395, filed on Mar. 15, 1999.

(51) Int. Cl.⁷ .................................................. A61C 15/00
(52) U.S. Cl. ........................ 132/329; 132/321; 206/104
(58) Field of Search ..................... 132/329, 321, 132/309; 206/104, 581

(56) References Cited

U.S. PATENT DOCUMENTS

| | | | |
|---|---|---|---|
| 2,006,678 | * 7/1935 | Kappler | 206/104 |
| 2,760,628 | 8/1956 | Briggs | 206/104 |
| 2,762,501 | 9/1956 | Cameron | 206/104 |
| 3,954,115 | 5/1976 | Bengtsson | 132/329 |
| 4,651,760 | 3/1987 | Reipur | 132/327 |
| 4,878,508 | * 11/1989 | Durbin | 132/329 |
| 4,998,978 | 3/1991 | Varnum | 606/130 |
| 5,016,659 | * 5/1991 | Mas | 132/321 |
| 5,119,941 | 6/1992 | Lepie | 206/102 |
| 5,560,379 | 10/1996 | Pieczenik | 132/329 |
| 5,682,912 | * 11/1997 | Desiderio | 132/329 |
| 5,855,215 | 1/1999 | Clarke | 132/321 |
| 5,875,798 | * 3/1999 | Petrus | 132/321 |
| 6,044,848 | * 4/2000 | Huang | 132/321 |

\* cited by examiner

*Primary Examiner*—John J. Wilson
*Assistant Examiner*—Melba Bumgarner
(74) *Attorney, Agent, or Firm*—William D. Hall

(57) ABSTRACT

A packet of toothpicks has a one-piece plastic sheet, folded onto itself to provide two layers of plastic toothpicks, each of which toothpicks has a handle portion and a cleaning portion. The cleaning portion is embossed to form a surface that will abrade plaque. Flavoring, or other chemical, may be placed in pockets or grooves formed in the embossed area.

11 Claims, 1 Drawing Sheet

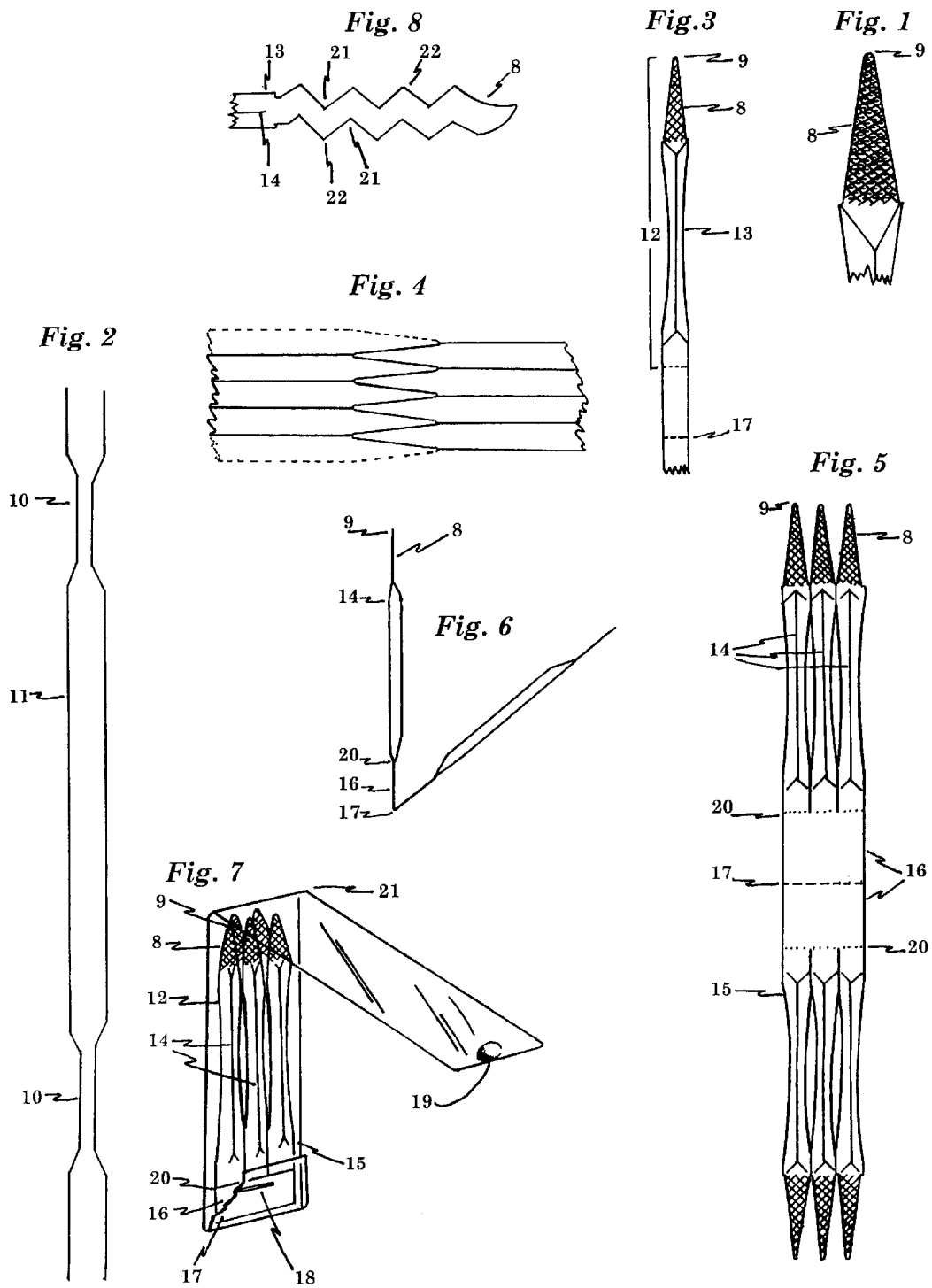

EXTRUDED PLASTIC TOOTHPICK AND METHOD

RELATED APPLICATION

This application claim the benefit of our prior now abandoned Provisional Application Serial No. 60/124,395, filed Mar. 15, 1999.

BACKGROUND OF THE INVENTION

Toothpicks are very old and have been the subject of patents for over a century. For example, U.S. patent to Briggs No. 2,760,628 granted Aug. 28, 1956 discloses a toothpick which consists of a body of thin and flexible plastic stock that is pointed at one end to provide a tip and has a longitudinal crimp extending substantially from end to end thereof but terminating short of the apex of the tip. Such a toothpick is longitudinally stiffened throughout the main part thereof, while its tip remains relatively flexible thereby enabling material costs to be held to a minimum and the toothpicks to have novel and advantageous characteristics.

More recently, U.S. patent to Varum, No. 4,998,978 teaches a cloth or plastic strip formed of crossed strands forming cross ridges in surfaces of a strip to produce a frictional scrubbing arrangement against teeth surfaces.

U.S. Pat. No. 3,954,115 to Bengtsson, granted May 4, 1976, teaches a toothpick having a channel-shaped cross-section tapering to a point, and a picking portion. Both portions are roughened along their sides and are partly roughened in order to provide an abrading surface.

It is also old and well known to provide flavoring to toothpicks, toothbrushes, etc.

SUMMARY OF THE INVENTION

Individual toothpicks as well as a packet of toothpicks, are made according to the invention.

Each toothpick has a handle portion and an embossed cleaning portion. The embossing renders the cleaning portion effective in cleaning between teeth and also provides pockets or grooves into which any suitable chemical such as flavoring may be placed.

The handle portion is thicker than the cleaning portion to provide strength.

The packet of toothpicks is made by a process which forms a sheet having a center portion and two outer portions. The center portion is folded onto itself so that half of that portion is contiguous with the other half. Therefore, the two outer portions are also contiguous with each other and ultimately are the cleaning portions of the toothpicks.

A cover having a side that may open and close encloses the above packet of toothpicks and has an adhesive for allowing the cover to be removably held in a closed position when the toothpicks are not being removed from the packet.

BRIEF DESCRIPTION OF THE DRAWINGS

FIG. 1 is an elevation view of the tip end of a toothpick embodying our invention.

FIG. 2 is a sectional view, of an extruded plastic strip from which our new toothpick is formed.

FIG. 3 is a view, in elevation, of our new toothpick.

FIG. 4 is a partial view, in elevation, showing a plurality of plastic strips from which a number of our toothpicks may be formed.

FIG. 5 is an elevational view of plastic strips from which a packet of toothpicks may be formed.

FIG. 6 is a side view, of the plastic strips of FIG. 5, showing how the strips are folded to form a group of toothpicks.

FIG. 7 is a perspective view of a packet of toothpicks embodying our invention.

FIG. 8 is a side view of the tooth-cleaning end of our new toothpick.

DETAILED DESCRIPTION OF THE INVENTION

The toothpicks 15 of this invention are preferably made from an extruded plastic strip having the cross-section shown in FIG. 2. The thicker portion 11, of the strip of FIG. 2, is preferably 0.015 inches thick and the thinner portion 10 is preferably 0.0125 inches thick. The handle portion 13 of the toothpick 15 is preferably stiff and the picking portion 8 is preferably somewhat soft. However, since the handle 13 and picking portion 8 are made in one piece a plastic is used that is a compromise so far as its hardness is concerned.

The extruded strip of FIG. 2 is next passed between calendaring rollers to form the strip into the shape shown in FIG. 5. The cleaning portion 8 and the rounded tip 9 are shown in FIG. 5. The cleaning portion 8 is embossed and indented by said rollers, or in a separate operation by striking the same with a die, to form a multiplicity of small geometric a raised projections 21, 22 as shown in FIG. 8, characterized by narrow channels or grooves or pockets adjacent the raised projections. The purpose of the narrow channels or grooves is to receive one or more of (a) flavoring, such as mint flavoring (b) mouth antiseptic and (c) sodium fluoride.

The calendar rolling step, or a separate crimping tie applies crimps 14 to the handles to thus strengthen and further stiffen the handles. At the same time the rolling step also gives the portion 8 a slight concave shape.

The next step in the process of making our final product is to separate the individual toothpicks by providing longitudinal slits between individual toothpicks 15.

The group of toothpicks of FIG. 5 is then folded along line 17 to form a base 16 which is then inserted into a cover 23 as shown in FIG. 7. Staple 18 is then passed through a two layers of cover 23 and through the double layer 16 of the group of plastic toothpicks to hold the entire packet of FIG. 7 together.

Finally, a small spot of adhesive 19 is applied to the cover 23 thereby holding the cover 23 closed until it is about to be used. Each of the six resulting toothpicks 15 in the packet 21 has a length of about 2.25 inches and a width of about 3/16 of an inch.

The reason that the handle portion 13 of the toothpick is thicker than the cleaning portion 8, as explained in connection with FIG. 2, is to give the handle portion 13 strength and to keep the cleaning portion 8 small enough so it will pass between the teeth to be cleaned.

At least one of the above steps involved in making the final product of FIG. 7, includes applying score lines 20 (FIG. 5) at the base line of the toothpicks 15 so that individual toothpicks 15 can be easily removed from the packet 21. Hence, the actual length of a toothpick is shown at 12 in FIG. 3.

While we illustrate a total of six toothpicks 15 per packet, a packet can have any desired number of toothpicks.

FIG. 8 shows one form that the embossing may take. In FIG. 8, projections 21 extend above and below the surface of the plastic strip and grooves or pockets are located adjacent the projections 21. In practice many more projections and grooves would be present on the cleaning portion 8 than are shown.

Instead of simple inverted V-shaped projections the embossing may take any other geometric form that extends above and below the plane of the surface of the plastic strip.

The invention not only provides a packet of toothpicks that is low in cost but also a low cost method for producing packets of toothpicks.

The adhesive 19 may be of the type that allows the cover of the packet to remain sealed. No toothpick can be used until the seal is broken thus insuring that no toothpicks have been used beforehand so that positive sanitation is maintained.

What is claimed is:

1. A method of making a toothpick adapted to be inserted between two teeth, comprising:

extruding a one-piece strip having a first portion thereof constituting a handle portion and a second portion joined to the handle portion and extending from said handle portion to an end of said one-piece strip, with said second portion constituting a cleaning portion of said one-piece strip, said extruding step forming said handle portion thicker than said cleaning portion and big enough so it may be easily held by a human hand and being long as compared to either its width or its thickness, and embossing at least part of said cleaning portion to form an embossed area which when inserted between two teeth tends to abrade or remove any material, on the surface of a tooth, that is engaged by said embossed area.

2. A method of making a toothpick as defined in claim 1, in which said embossing step comprises forming a plurality of spaced projections.

3. A method of making a toothpick as defined in claim 2, in which said step of forming projections comprises forming pockets or grooves between said projections.

4. A method of making a toothpick as defined in claim 3 comprising, providing a chemical in said pockets or grooves that will be imparted to the mouth of the person using the toothpick.

5. A method of making a packet of toothpicks in which each of which toothpicks is adapted to be inserted between two teeth for not only removing objects located between the two teeth but also for tending to clean the portions of the two teeth that face each other, comprising:

forming an elongated one-piece member and folding it back onto itself to provide top and bottom layers each of which layers is at least one toothpick, providing each layer with a base portion, a handle portion and a cleaning portion, said folding step positioning the base portion of the top layer contiguous with the base portion of the bottom layer, said folding step positioning the handle portion of the top layer contiguous with the handle portion of the other layer, providing a cleaning portion for each layer with an abrasive surface, and providing a one piece cover for the packet contiguous with both base portions, and further extending contiguous with a handle portion of said bottom layer, folding said cover also having by 180 degrees thereby providing a front portion, and connecting said cover, and said one-piece member together to form a unitary device, while leaving at least a Dart of said front portion free to swing between open and closed positions.

6. A method of making a packet of toothpicks as defined in claim 5, comprising forming said front portion to overlap that part of said cover which is contiguous with both of said base portions, and providing an adhesive on said cover to removably hold the cover in a closed position.

7. A method as defined in claim 5 in which said forming step is carried out by extruding said one-piece member.

8. A packet of toothpicks each of which toothpicks is adapted to be inserted between two teeth, comprising:

an elongated one-piece member folded back onto itself to provide top and bottom layers each of which layers is at least one toothpick, each layer comprising a base portion, a handle portion and a cleaning portion, the base portion of the top layer lying contiguously with the base portion of the bottom layer, the handle portion of the top layer lying contiguously with the handle portion of the bottom layer, the cleaning portion of the top layer lying contiguously with the cleaning portion of the other layer, the cleaning portion of each layer having an abrasive surface, and a one-piece cover for the packet contiguous with both base portions, further extending contiguous with the handle portion of said bottom layer, and with a cleaning portion of said bottom layer, said one-piece cover also having a 180 degree fold and having a front portion that forms the front of the packet, removably positioned contiguously with a handle portion and a cleaning portion of said top layer, and said cover and said one-piece member being connected together to form a unitary device and wherein said front portion may swing between open and closed positions, said front portion extending to and overlapping that part of said cover which is contiguous with said base portions, and means on said cover to removably hold the cover in a closed position said means being an adhesive that tends to hold the cover sealed and in a closed position until said seal is broken thus tending to maintain the contents of the packet in a sanitary condition.

9. The method of making toothpicks comprising:

providing an elongated strip of plastic material, forming said strip to provide a center portion of said strip and two end portions with said center portion positioned between said two end portions, so that said strip extends longitudinally from one of its ends along one of said end portions, said center portion and the other end portion, folding about half of said strip along a first line perpendicular to said longitudinal direction until half of said center portion lies contiguous with the other half of said center portion thereby placing said two end portions in an adjacent relationship, said forming step including extrading said center portion thicker than said end portions, said forming step also scoring said center portion along second and third lines one on each side of and parallel to said first line and wherein the second and third lines are each spaced from said first line.

10. The method of making toothpicks comprising:

providing an elongated strip of plastic material, forming said strip to provide a center portion of said strip and two end portions with said center portion positioned between said two end portions, so that said strip extends longitudinally from one of its ends along, one of said end portions, said center portion and the other end portion, folding about half of said strip along a first line perpendicular to said longitudinal direction until half of said center portion lies contiguous with the other half of said center portion, and so that said two end portions and are contiguous said forming step forming a center portion thicker than said end portions, said forming step also scoring said center portion along second and third lines one on each side of and parallel to said first line and wherein the second and third lines are each spaced from said first line, and embossing said two end portions.

11. A packet of toothpicks each of which toothpicks is adapted to be inserted between two teeth, comprising:

an elongated one-piece member folded back onto itself to provide top and bottom layers each of which layers is at least one toothpick, each layer comprising a base portion, a handle portion and a cleaning portion; the base portion of the top layer lying contiguously with the base portion of the bottom layer, the handle portion of the top layer lying contiguously with the handle portion of the bottom layer, the cleaning portion of the top layer lying contiguously with the cleaning portion of the bottom layer, the cleaning portion of each layer having an abrasive surface, and a one-piece cover for the packet contiguous with both base portions, further extending contiguous with the handle portion of said bottom layer, and with a cleaning portion of said bottom layer, said one-piece cover is an elongated sheet, said sheet having two 180 degree folds therein, each said fold being along a line perpendicular to the length of said elongated sheet, said lines being spaced apart a distance equal to the height of said packet, said packet having a front side and a back side; said back side comprising a continuous portion of said sheet, said front side comprising two flaps one of which is longer than the other and which overlaps said other flap, said cover and said one-piece member being connected together to form a unitary device and wherein said front side may swing between open and closed positions, and means on said cover to removably hold the cover in a closed position, said means being an adhesive that tends to hold the cover sealed and in a closed position until said seal is broken thus tending to maintain the contents of the packet in a sanitary condition.

* * * * *